United States Patent [19]
Oe et al.

[11] Patent Number: 4,808,620
[45] Date of Patent: Feb. 28, 1989

[54] PYRAZOLOPYRIDINE COMPOUNDS, THEIR PREPARATION AND USE AS PLATELET AGGREGATION INHIBITORS

[75] Inventors: Takanori Oe, Oita; Kazuyuji Kawasaki, Fukuoka; Michio Terasawa; Tomonori Imayoshi, both of Oita; Yukihiro Yasunaga, Fukuoka, all of Japan

[73] Assignee: Yoshitomi Pharmaceutical Industries, Ltd., Osaka, Japan

[21] Appl. No.: 76,504

[22] Filed: Jul. 22, 1987

[30] Foreign Application Priority Data

Jul. 22, 1986 [JP] Japan ................................ 61-172479

[51] Int. Cl.$^4$ .................. A61K 31/38; A61K 31/395; A61K 31/435; C07D 471/04
[52] U.S. Cl. ................................. 514/303; 514/228.5; 514/231.5; 514/254; 546/119; 546/120; 544/405; 544/408; 544/409; 544/362; 544/125; 544/61
[58] Field of Search ................. 546/119, 120; 514/303, 514/254

[56] References Cited

U.S. PATENT DOCUMENTS

| 3,925,388 | 12/1975 | Hoehn et al. | 546/119 |
| 4,535,165 | 8/1985 | Moore | 546/119 |
| 4,636,516 | 1/1987 | Kubo et al. | 546/120 |

FOREIGN PATENT DOCUMENTS

| 0104522 | 4/1984 | European Pat. Off. | 546/119 |
| 57-21375 | 2/1982 | Japan | 546/119 |
| 57-175171 | 10/1982 | Japan | 546/119 |
| 58-148858 | 9/1983 | Japan | 546/119 |
| 8301775 | 5/1983 | PCT Int'l Appl. | 546/119 |

OTHER PUBLICATIONS

Chemical & Pharmaceutical Bulletin, vol. 31, No. 9, pp. 3168-3185 (1983).
Chemical & Pharmaceutical Bulletin, vol. 32, No. 1, pp. 152-165 (1984).
Patent Abstracts of Japan, vol. 7, No. 268 citing Japanese Patent Appln. JP-A-58-148858, published 9/5/83.
Chemical abstract, vol. 92, No. 17, Apr. 28, 1980, p. 583, Abstract No. 146665s.
Chemical Abstract, vol. 84, No. 15, Apr. 12, 1976, p. 568, Abstract No. 105473u.

Primary Examiner—Mary C. Lee
Assistant Examiner—J. Richter
Attorney, Agent, or Firm—Sughrue, Mion, Zinn, Macpeak, and Seas

[57] ABSTRACT

A pyrazolopyridine compound of the formula:

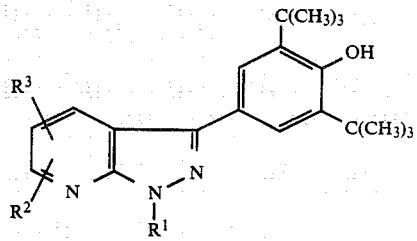

or a salt thereof, wherein each symbol is as defined in the specification.

Said compounds exhibit antiinflammatory, analgesic, antipyretic, antiallergic, antiarthritic, antirheumatic activities or inhibitory activities on platelet aggregation.

4 Claims, No Drawings

PYRAZOLOPYRIDINE COMPOUNDS, THEIR PREPARATION AND USE AS PLATELET AGGREGATION INHIBITORS

FIELD OF THE INVENTION

The present invention relates to the novel and pharmaceutically valuable pyrazolopyridine compounds and salts thereof, their preparation and use.

DESCRIPTION OF THE PRIOR ART 3,5-Di-tertiary butyl-4-hydroxyphenyl-substituted-pyrazole compounds which have antiinflammatory, analgesic and antipyretic activities are disclosed in Japanese Patent Application Publication (Unexamined) No. 148858/1983.

SUMMARY OF THE INVENTION

The present inventors have been intensively investigated to develop useful compounds as potent medicines, in particular, as antiinflammatory agents, analgesics, anti-pyretic agents, antiallergic agents, antiarthritic agents, antirheumatic agents or platelet aggregation inhibitors.

The present inventors have found that novel pyrazolopyridine compounds exhibit such potent activities as described above, and completed the present invention.

The present invention, namely, relates to the pyrazolopyridine compounds of the formula:

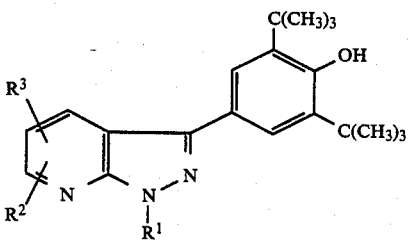

and salts thereof.

In the above formula, $R^1$ is hydrogen, alkyl, alkenyl, alkynyl, cycloalkyl, phenyl, substituted phenyl, heteroaryl, substituted heteroaryl, haloalkyl, hydroxyalkyl, alkoxyalkyl, acyloxyalkyl, carboxyalkyl, alkoxycarbonylalkyl, cyanoalkyl, carbamoylalkyl, mono- or di-substituted carbamoylalkyl, alkoxycarbonyloxyalkyl, carbamoyloxyalkyl, mono- or di-substituted carbamoyloxyalkyl, alkylthioalkyl, phenylalkyl, substituted phenylalkyl, heteroarylalkyl, substituted heteroarylalkyl, cycloalkylalkyl, a group of the formula:

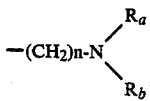

where each of $R_a$ and $R_b$ is hydrogen, alkyl, phenylalkyl, substituted phenylalkyl, or $R_a$ and $R_b$ together with the nitrogen atom form a heterocycle, and n is an integer of 1 to 8; alkanoyl, alkoxycarbonyl, acyloxyalkanoyl, benzoyl, substituted benzoyl, heteroarylcarbonyl, substituted heteroarylcarbonyl or a group of the formula:

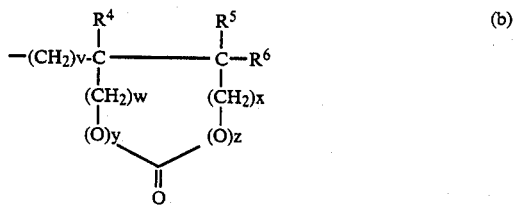

where each of $R^4$, $R^5$ and $R^6$ is hydrogen or alkyl, or $R^4$ and one of $R^5$ or $R^6$ together form a single bond, and each of v, w, x, y and z is an integer of 0 and 1 to 4; and each of $R^2$ and $R^3$ is hydrogen, halogen, alkyl or haloalkyl.

DETAILED DESCRIPTION OF THE INVENTION

In the above definitions and the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

alkenyl means straight or branched chain alkenyl having 2 to 8 carbon atoms, and includes, for example, vinyl, 1-propenyl, allyl, isopropenyl, 2-butenyl, 1,3-butanedienyl, 2-pentenyl, 2-hexenyl and octenyl;

alkynyl means straight or branched chain alkynyl having 2 to 8 carbon atoms, and includes, for example, ethynyl, 2-propynl, butynyl, pentynyl, hexynyl, heptynyl and octynyl;

substituted phenyl means phenyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

heteroaryl means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl;

substituted heteroaryl means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

haloalkyl means straight or branched chain alkyl having 1 to 10 carbon atoms which is substituted at least one halogen as mentioned above;

hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3-dihydroxypropyl, 1,3-dihydroxy-2-propyl;

alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl and 8-octyloxyoctyl;

acyloxyalkyl means that the acyl moiety is alkanoyl having 2 to 18 carbon atoms, benzoyl, substituted benzoyl, heteroarylcarbonyl or substituted heteroarylcarbonyl and the alkyl moiety is straight or branched chain alkyl having 1 to 8 carbon atoms, and includes, for example, acetoxymethyl, 2-acetoxyethyl, 3-acetoxypropyl, 4-acetoxybutyl, 6-acetoxyhexyl, 8-acetoxyoctyl, propionyloxymethyl, 2-propionyloxyethyl, 3-propionyloxypropyl, 4-propionyloxybutyl, 6-propionyloxyhexyl, 8-propionyloxyoctyl, isobutyryloxymethyl, 2-isobutyryloxyethyl, 4-isobutyryloxybutyl, pivaloyloxymethyl, 2-pivaloyloxyethyl, 4-pivaloyloxybutyl, butyryloxymethyl, 2-butyryloxyethyl, 4-butyryloxybutyl, valeryloxymethyl, 2-valeryloxyethyl, 4-valeryloxybutyl, hexanoyloxymethyl, 2-hexanoyloxyethyl, 4-hexanoyloxybutyl, octanoyloxymethyl, 2-octanoyloxyethyl, 4-octanoyloxybutyl, lauroyloxymethyl, 2-lauroyloxyethyl, 4-lauroyloxybutyl, stearoyloxymethyl, 2-stearoyloxyethyl, 4-stearoyloxybutyl, benzoyloxymethyl, 2-benzoyloxyethyl, 4-benzoyloxybutyl, furoyloxymethyl, 2-furoyloxyethyl, 4-furoyloxybutyl, thenoyloxymethyl, 2-thenoyloxyethyl, 4-thenoyloxybutyl, nicotinoyloxymethyl, 2-nicotinoyloxyethyl and 4-nicotinoyloxybutyl;

carboxyalkyl means that the alkyl moiety is straight or branched chain alkyl having 1 to 8 carbon atoms and includes, for example, carboxymethyl, 2-carboxymethyl, 3-carboxypropyl, 4-carboxybutyl, 6-carboxyhexyl and 8-carboxyoctyl;

alkoxycarbonylalkyl means that the alkoxy moiety and the alkyl moiety each are straight or branched chain ones having 1 to 8 carbon atoms, and includes, for example, methoxycarbonylmethyl, ethoxycarbonylmethyl, propoxycarbonylmethyl, isopropoxycarbonylmethyl, butoxycarbonylmethyl, isobutoxycarbonylmethyl, tertiary butoxycarbonylmethyl, pentlyoxycarbonylmethyl, hexyloxycarbonylmethyl, octyloxycarboylmethyl, 2-methoxycarbonylethyl, 2-ethoxycarbonylethyl, 2-propoxycarbonylethyl, 2-butoxycarbonylethyl, 3-methoxycarbonylpropyl, 3-ethoxycarbonylpropyl, 3-propoxycarbonylpropyl, 3-butoxycarbonylpropyl, 4-methoxycarbonylbutyl, 4-ethoxycarbonylbutyl, 4-propoxycarbonylbutyl, 4-butoxycarboylbutyl, 6-methoxycarbonylhexyl, 6-ethoxycarbonylhexyl, 8-methoxycarbonyloctyl and 8-ethoxycarbonyloctyl;

cyanoalkyl means that the alkyl moiety is straight or branched chain alkyl having 1 to 8 carbon atoms and includes, for example, cyanomethyl, 2-cyanoethyl, 3-cyanopropyl, 4-cyanobutyl, 6-cyanohexyl and 8-cyanooctyl;

carbamoylalkyl means that the alkyl moiety is straight or branched chain alkyl having 1 to 8 carbon atoms and includes, for example, carbamoylmethyl, 2-carbamoylethyl, 3-carbamoylpropyl, 4-carbamoylbutyl, 6-carbamoylhexyl and 8-carbamoyloctyl;

mono- or di-substituted carbamoylalkyl means that the substituent(s) to the nitrogen atom of the carbamoyl moiety is(are) selected from the group consisting of hydrogen, straight or branched chain alkyl having 1 to 8 carbon atoms, phenylalkyl, substituted phenylalkyl and 5 to 10 membered mono- or fused-heterocycle that may optionally have at least one heteroatom selected from the group consisting of nitrogen which may be optionally substituted, oxygen and sulfur to be formed together with the adjacent nitrogen atom, and the alkyl moiety is straight or branched chain alkyl having 1 to 8 carbon atoms, and includes, for example, N-methylcarbamoyl, N-ethylcarbamoyl, N-butylcarbamoyl, N-benzylcarbamoyl, N,N-dimethylcarbamoyl, N,N-diethylcarbamoyl, 1-pyrrolidinylcarbonyl, 2-oxo-1-pyrrolidinylcarbonyl, piperidinocarbonyl, 4-methyl-1-piperazinylcarbonyl, 4-(2-hydroxyethyl)-1-piperazinylcarbonyl and morpholinocarbonyl;

alkoxycarbonyloxyalkyl means that the alkoxy moiety and the alkyl moiety each are straight or branched chain ones having 1 to 8 carbon atoms, and includes, for example, methoxycarbonyloxymethyl, ethoxycarbonyloxymethyl, propoxycarbonyloxymethyl, butoxycarbonyloxymethyl, isobutoxycarbonyloxymethyl, hexyloxycarbonyloxymethyl, octyloxycarbonyloxymethyl, 2-methoxycarbonyloxyethyl, 2-ethoxycarbonyloxyethyl, 1-ethoxycarbonyloxyethyl, 2-butoxycarbonyloxyethyl, 3-methoxycarbonyloxypropyl, 3-ethoxycarbonyloxypropyl, 3-butoxycarbonyloxypropyl, 4-methoxycarbonyloxybutyl, 4-ethoxycarbonyloxybutyl and 4-butoxycarbonyloxybutyl;

carbamoyloxyalkyl means that the alkyl moiety is straight or branched chain alkyl having 1 to 8 carbon atoms and includes, for example, carbamoyloxymethyl, 2-carbamoyloxyethyl, 3-carbamoyloxypropyl, 4-carbamoyloxybutyl, 6-carbamoyloxyhexyl and 8-carbamoyloxyoctyl;

mono- or di-substituted carbamoyloxyalkyl means that the substituent(s) to the nitrogen atom of the carbamoyl moiety is(are) selected from the group consisting of hydrogen, straight or branched chain alkyl having 1 to 8 carbon atoms, phenylalkyl, substituted phenylalkyl and 5 to 10 membered mono- or fused heterocycle that may optionally have at least one heteroatom selected from the group consisting of nitrogen which may be optionally substituted, oxygen and sulfur to be formed together with the adjacent nitrogen atom, and the alkyl moiety is straight or branched chain alkyl having 1 to 8 carbon atoms, and includes, for example, N-methylcarbamoylxoymethyl, N-ethylcarbamoyloxymethyl, N-butylcarbamoyloxymethyl, N-benzylcarbamoyloxymethyl, 2-(N-methylcarbamoyloxy)ethyl, 2-(N-ethylcarbamoyloxy)ethyl, 2-(N-benzylcarbamoyloxy)ethyl, 3-(N-methylcarbamoyloxy)propyl, 3-(N-ethylcarbamoyloxy)propyl, 3-(N-butylcarbamoyloxy)propyl, 4-(N-methylcarbamoyloxy)butyl, 4-(N-ethylcarbamoyloxy)butyl, 4-(N-butylcarbamoyloxy)butyl, N,N-dimethylcarbamoyloxymethyl, 2-(N,N-dimethylcarbamoyloxy)ethyl, 4-(N,N-dimethylcarbamoyl-oxy)butyl, N,N-diethylcarbamoyloxymethyl, 2-(N,N-diethylcarbamoyloxy)ethyl, 4-(N,N-diethylcarbamoyloxy)butyl, 1-pyrrolidinylcarbonyloxymethyl, 2-(1-pyrrolidinylcarbonyloxy)ethyl, 4-(1-pyrrolidinylcarbonyloxy)butyl, 6-(1-pyrrolidinylcarbonyloxy)hexyl, 2-oxo-1-pyrrolidinylcarbonyloxymethyl, 2-(2-oxo-1-pyrrolidinylcarbonyloxy)ethyl, 4-(2-oxo-1-pyrrolidinylcarbonyloxy)butyl, piperidinocarbonyloxymethyl, 2-piperidinocarbonyloxyethyl, 4-piperidinocarbonyloxybutyl, 4-methyl-1-piperazinylcarbonyloxymethyl, 2-(4-methyl-1-piperazinylcarbonyloxy)ethyl, 4-(4-methyl-1-piperazinylcarbonyloxy)butyl, 4-(2-hydroxyethyl)-1-piperazinylcarbonyloxymethyl, 2-(4-(2-hydroxyethyl)-1-piperazinylcarbonyloxy)ethyl, 4-(4-(2-hydroxyethyl)-1-piperazinylcarbonyloxy)butyl, morpholinocarbonyloxymethyl, 2-morpholinocarbonyloxyethyl and 4-morpholinocarbonyloxybutyl;

alkylthioalkyl means that the alkylthio moiety and the alkyl moiety each are straight or branched chain ones having 1 to 8 carbon atoms and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 4-butylthiobutyl, 6-methylthiohexyl, 6-ethylthiohexyl, 6-butylthiohexyl, 8-methylthiooctyl, 8-ethylthiooctyl and 8-butylthiooctyl;

phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl;

substituted phenylalkyl means above-mentioned phenylalkyl which is substituted by at least one substituent selected from the group consisting of halogen, amino, nitro, hydroxy, alkyl, alkoxy and haloalkyl on the phenyl nucleus;

heteroarylalkyl means that the heteroaryl moiety is 5 to 10 membered mono- or fused-heteroaromatic ring having at least one heteroatom selected from the group consisting of nitrogen, oxygen and sulfur as mentioned above and the alkyl moiety is straight or branched chain alkyl having 1 to 8 carbon atoms, and includes, for example, furfuryl, 3-furylmethyl, 2-thenyl, 3-thenyl, 2-, 3- or 4-pyridylmethyl, pyrazolylmethyl, 1-imidazolylmethyl, pyrimidinylmethyl, benzimidazolylmethyl, 2-(2-furyl)ethyl, 2-(2-thienyl)ethyl, 2-(2-pyridyl)ethyl, 2-(1-imidazolyl)ethyl, 3-(2-furyl)propyl, 3-(2-thienyl)propyl, 3-(2-pyridyl)propyl, 4-(2-furyl)butyl, 4-(2-thienyl)butyl and 4-(2-pyridyl)butyl;

substituted heteroarylalkyl means that the substituted heteroaryl moiety is 5 to 10 membered mono- or fused-heteroaromatic ring which is substituted by at least one substituent selected from the group consisting of halogen, amino, nitro, hydroxy, alkyl, alkoxy and haloalkyl on the heteroaryl nycleus and which has at least one heteroatom selected from the group consisting of nitrogen, oxygen and sulfur as mentioned above, and that the alkyl moiety is straight or branched chain alkyl having 1 to 8 carbon atoms;

cycloalkylalkyl means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl and 6-cyclohexylhexyl;

in the group of formula (a), the heterocycle to be formed by $R_a$ and $R_b$ together with the adjacent nitrogen atom means 5 to 10 membered mono- or fused-heterocycle that may optionally contain at least one heteroatom selected from the group consisting of oxygen, sulfur and nitrogen which may optionally be substituted by alkyl, hydroxyalkyl, phenylalkyl or substituted phenylalkyl, and includes, for example, 1-pyrrolidinyl, 2-oxo-1-pyrrolidinyl, piperidino, 1-piperazinyl, 4-methyl-1-piperazinyl, 4-(2-hydroxyethyl)-1-piperazynyl, 4-benzylpiperazinyl, 1-homopiperazynyl, morpholino and thiomorpholino;

alkanoyl means alkanoyl having 2 to 18 carbon atoms and includes, for example, acetyl, propionyl, butyryl, isobutyryl, pivaloyl, valeryl, hexanoyl, octanoyl, lauroyl and stearoyl;

alkoxycarbonyl means that the alkoxy moiety is alkoxy having 1 to 10 carbon atoms and includes, for example, methoxycarbonyl, ethoxycarbonyl, propoxycarbonyl, isopropoxycarbonyl, butoxycarbonyl, isobutoxycarbonyl, tertiary butoxycarbonyl, pentyloxycarbonyl, hexyloxycarbonyl, heptyloxycarbonyl, octyloxycarbonyl, nonyloxycarbonyl and decyloxycarbonyl;

acyloxyalkanoyl means that the acyl moiety is alkanoyl having 2 to 18 carbon atoms, benzoyl, substituted benzoyl, heteroarylcarbonyl or substituted heteroarylcarbonyl as mentioned above and the alkanoyl moiety is alkanoyl having 2 to 18 carbon atoms;

substituted benzoyl means benzoyl which is substituted by at least one substituent selected from the group consisting of halogen, amino, nitro, hydroxy, alkyl, alkoxy and haloalkyl on the benzene ring;

heteroarylcarbonyl means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thenoyl, nicotinoyl, isonicotinoyl, pyrazolylcarbonyl, imidazolylcarbonyl, pyrimidinylcarbonyl and benzimidazolylcarbonyl;

substituted heteroarylcarbonyl means the above-mentioned heteroarylcarbonyl which is substituted by at least one substituent selected from the group consisting of halogen, amino, nitro, hydroxy, alkoxy and haloalkyl on the heteroaryl nucleus; and the group of formula (b) includes, for example, 2-oxo-1,3-dioxolan-4-ylmethyl, 2-oxo-1,3-dioxan-5-yl, 2-oxo-3-tetrahydrofurfuryl, 4-methyl-2-oxo-1,3-dioxol-5-ylmethyl and 4-methyl-2-oxo-1,3-dioxolan-4-yl.

The present invention embraces any of racemates and individual optical isomers thereof of the compounds of formula (I) having a chiral carbon atom.

The salts of the compounds of formula (I) include pharmaceutically acceptable salts such as inorganic acid addition salts (e.g. hydrochloride, hydrobromide, sulfate, nitrate or phosphate), organic acid addition salts (e.g. acetate, tartrate, citrate, fumarate, maleate, mandelate, oxalate, salicylate, hybenzate, fendizoate, methanesulfonate or p-toluenesulfonate), metallic salts (e.g. sodium salt, potassium salt, calcium salt, magnesium salt or aluminum salt), salts with bases (e.g. salt with triethylamine, diethanolamine, ammonium, guanidine, hydrazine, quinine or cinchonin) or salts with amino acids (e.g. salt with lysine or glutamine).

The compounds of formula (I) of the present invention can be, for example, prepared by reacting a compound of the formula:

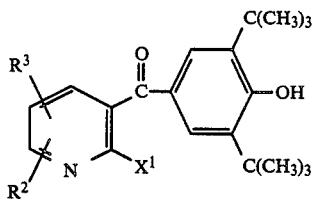
(II)

wherein $X^1$ is halogen and other symbols are as defined above, with a compound of the formula:

$R^1-NHNH_2$ (III)

wherein $R^1$ is as defined above, or hydrate thereof.

The reaction is usually carried out at a temperature from room temperature to the boiling point of the solvent employed for 1 to 24 hours in the presence or absence of a base (e.g. sodium hydroxide, potassium hydroxide, sodium carbonate, potassium carbonate, sodium hydrogencarbonate, sodium hydride, sodium methoxide, sodium ethoxide or sodium amide) in an inert solvent (e.g. methanol, ethanol, benzene, toluene, acetone, dimethylformamide, dimethylsulfoxide, hexamethylphosphoric triamide, pyridine or N-methyl-2-pyrrolidone or mixtures thereof).

The compounds of formula (I) can also be prepared by separating a hydrazone compound of the formula:

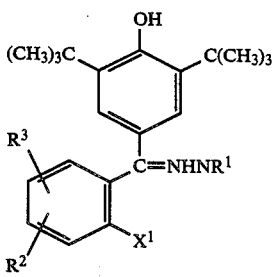
(IV)

wherein each symbol is as defined above, as an intermediate in the course of the above reaction and then subjecting the compounds of formula (IV) in the presence of the above-mentioned base to the ring closure reaction.

The compounds of formula (I) wherein $R^1$ is other than hydrogen can be, for example, prepared by reacting a compound of the formula (I) wherein $R^1$ is hydrogen, i.e. a compound of the formula:

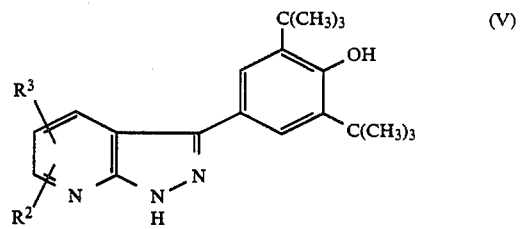
(V)

wherein each symbol is as defined above, with a compound of the formula:

$R_a^1-X^2$ (VI)

wherein $R_a^1$ is other than hydrogen in the definitions of $R^1$ and $X^2$ is a reactive atom or group (e.g. halogen, or methanesulfonyloxy, benzenesulfonyloxy or p-toluenesulfonyloxy).

The reaction is usually carried out at room temperature or under heating for 1 to 24 hours in, preferably, the presence of a base (e.g. sodium hydroxide, potassium hydroxide, sodium carbonate, potassium carbonate, sodium hydrogencarbonate, sodium hydride, sodium methoxide, sodium ethoxide or sodium amide) in an inert solvent (e.g. methanol, ethanol, benzene, toluene, acetone, dimethylformamide, dimethylsulfoxide, hexamethylphosphoric triamide or N-methyl-2-pyrrolidone, or mixtures thereof).

Further the compounds of formula (I) wherein $R^1$ is acyloxyalkyl, alkoxycarbonyoxylalkyl, carbamoyloxyalkyl, or mono- or di-substituted carbamoyloxyalkyl can be prepared by reacting a compound of the formula (I) wherein $R^1$ is hydroxyalkyl, i.e. a compound of the formula:

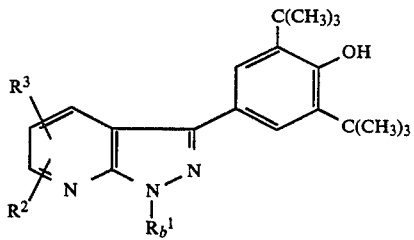
(VII)

wherein $R_b^1$ is hydroxyalkyl in the definitions of $R^1$ and other symbols are as defined above, with an acid halide (e.g. an acid chloride or an acid bromide), an acid anhydride, a mixed acid anhydride, a carbonic acid ester, a halocarbonate (e.g. chlorocarbonate), an isocyanate, a carbamyl halide (e.g. carbamyl chloride) or a mono- or di-substituted carbamyl halide.

The reaction of the compounds of formula (VII) with acid halide, acid anhydride, halocarbonate or carbamyl halide is usually carried out at 0°–150° C. for 1 to 24 hours in, preferably, the presence of a base (e.g. triethylamine, N-methylmorpholine, N-ethylmorpholine or pyridine) in an inert solvent (e.g. chloroform, dichloroethane, tetrahydrofuran, ethyl acetate, dimethylformamide., benzene or toluene, or mixtures thereof). The reaction with carbonate is carried out preferably in the presence of a base (e.g. sodium carbonate, potassium carbonate, sodium hydride, sodium methoxide, sodium ethoxide or sodium amide) and, if necessary, in an inert solvent (e.g. benzene, toluene, dimethylformamide or hexamethylphosphoric triamide), and the reaction with isocyanate is carried out in an inert solvent.

The compounds of formula (I) wherein $R^1$ is carbamoylalkyl, mono- or di-substituted carbamoylalkyl, or alkoxycarbonylalkyl can be prepared by reacting a compound of the formula (I) wherein $R^1$ is carboxyalkyl or a functional derivative thereof in the carboxy group, i.e. a compound of the formula:

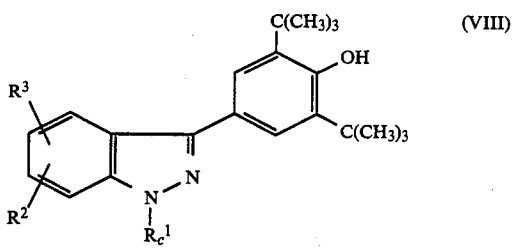
(VIII)

wherein $R_c^1$ is carboxyalkyl and other symbols are as defined above, or a functional derivative thereof in the carboxy group with a compound of the formula:

(IX)

wherein each of $R^7$ and $R^8$ is hydrogen, alkyl, phenylalkyl or substituted phenylalkyl, or $R^7$ and $R^8$ together with the adjacent nitrogen atom form a heterocycle, or a compound of the formula:

$R^9$—OH (X)

wherein $R^9$ is alkyl.

The functional derivatives of the compounds of formula (VIII) include, for example, an acid halide, an acid anhydride, a mixed acid anhydride (e.g. a mixed acid anhydride with carbonate such as ethyl carbonate or ethyl chlorocarbonate, or alkylphosphate), an active ester (e.g. p-nitrophenyl ester) or an amide (e.g. an amide with imidazole, succinimide or 2-thioxothiazolidine).

The reaction is usually carried out under cooling, at room temperature or under heating for 1 to 24 hours in an inert solvent (e.g. water, benzene, toluene, acetone, tetrahydrofuran, hydrofuran, dimethylformamide or ethyl acetate, or mixtures thereof) and if necessary, in the presence of a base (e.g. sodium hydroxide, potassium hydroxide, sodium carbonate, potassium carbonate, sodium hydrogencarbonate, triethylamine, N-methylmorpholine or N-ethylmorpholine) or a dehydration agent (e.g. dicyclohexylcarbodiimide, carbonyldiimidazole, diethyl cyanophosphonate or diphenylphosphoryl azide).

Furthermore, the compounds of formula (I) wherein $R^1$ is acyloxyalkyl, alkoxyalkyl, cyanoalkyl, alkylthioalkyl or the group of formula (a) can be prepared by reacting a compound of the formula (I) wherein $R^1$ is haloalkyl, i.e., a compound of the formula:

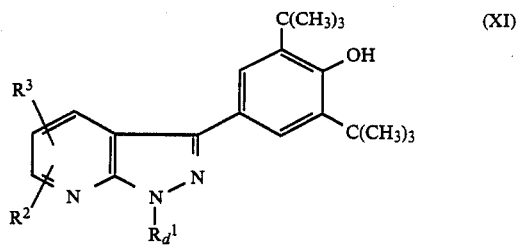
(XI)

wherein $R_d^1$ is haloalkyl and other symbols are as defined above, with a metal salt (e.g. sodium, potassium or calcium salts) of the corresponding carboxylic acid, alcohol, cyanide or mercaptan or a compound of the formula:

(XII)

wherein $R_a$ and $R_b$ are as defined above.

The reaction is usually carried out at room temperature or under heating for 1 to 24 hours in an inert solvent (e.g. methanol, ethanol, chloroform, benzene, toluene, acetone, tertahydrofuran, dimethylformamide or dimethylsulfoxide, or mixtures thereof). The reaction with the amino compound of formula (XII) is preferably carried out by using two equivalent amounts of the amine compound, or in the presence of another base (e.g. sodium hydroxide, potassium hydroxide, sodium carbonate, potassium.carbonate, sodium hydride, sodium amide, triethylamine, N-methylmorpholine or N-ethylmorpholine).

The salts of the compounds of formula (I) can be obtained in the course of the preparation of the compounds of formula (I), or, if desired, by converting to the above-mentioned pharmaceutically acceptable acid addition salts with an acid, an alkali, a base or an amino acid in a conventional manner.

The compounds of formula (I) of the present invention thus obtained can be separated by employing a conventional separation and purification procedure such as extraction, concentration, neutralization, filtration, recrystallization, column chromatography or thin layer chromatography from the reaction mixture.

The compounds of formula (I) having an asymmetric carbon is usually formed as racemates. Thus obtained racemates can be led to individual optical isomers by forming salts with an optically active acid (e.g. mandelic acid, tartaric acid, dibenzoyltartaric acid or 10-camphorsulfonic acid) or an optically active base (e.g. cinchonine, cinchonidine, quinine, quinidine, α-methylbenzylamine or dehydroabiethylamine), or by separating with chromatography or fractional recrystallization. The optically active isomers can also be prepared by using optically active starting compounds.

The starting compounds of formula (II) can, for example, be prepared by reacting a compound of the formula:

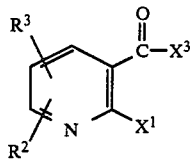

(XIII)

wherein $X^3$ is halogen and other symbols are as defined above, with 2,6-di-tertiary butyl phenol under the condition of Friedel-Crafts reaction, i.e., in the presence of a catalyst (e.g. aluminum chloride, ferric chloride, stannic chloride or zinc chloride) in an inert solvent (e.g. dichloroethane, tetrachloroethane, carbon disulfide or nitrobenzene).

Since the compounds of formula (II) are novel compounds, the present invention also provides the compounds of formula (II) which are industrially useful as intermediates to the novel and pharmaceutically valuable compounds of formula (I).

The pyrazolopyridine compounds of formula (I) and salts thereof of the present invention not only inhibit both cyclooxygenase and 5-lipoxygenase but also exhibit potent antiinflammatory activity, analgesic activity, antipyretic activity, antiallergic activity, antiarthritic activity, antirheumatic activity or inhibitory activity on platelet aggregation, and are useful as drugs such as antiinflammatory agents, analgesics, antipyretic agents, antiallergic agents, antiarthritic agents, antirheumatic agents or platelet aggregation inhibitors.

When the compounds of the present invention and the pharmaceutically acceptable salts thereof are used as drugs, they can be orally or parenterally administered alone or in the form of powder, granules, tablets inclusive of film-coated tablets and sugar coated tablets, capsules, injections, drip infusions, suppositories, ointments, cataplasms or eye drops prepared by admixing with pharmaceutically acceptable carriers, vehicles or diluents to patients in need of therapy. The dose may vary depending upon the diseases to be treated, the conditions of patient, the age of patient or way of administration, and in case of oral administration, the daily dose for human adults ranges from 1 to 1,000 mg, preferably from 50 to 500 mg in one to several times divided doses.

The following are the results of pharmacological experiments exhibiting the effectiveness of the pyrazolopyridine compounds (I) or their salts of the present invention.

The test compounds employed in the following experiments are as follows:

Compound A: 3-(3,5-di-tertiary butyl-4-hydroxyphenyl)-1-methyl-1H-pyrazolo[3,4-b]pyridine Compound B: 3-(3,5-di-tertiary butyl-4-hydroxyphenyl)-1-(2-hydroxyethyl)-1H-pyrazolo [3,4-b]pyridine Compound C: 3-(3,5-di-tertiary butyl-4-hydroxyphenyl)-1-(2'propionyloxyethyl)-1H-pyrazolo [3,4-]pyridine Compound D: 3-(3,5-di-tertiary butyl-4-hydroxyphenyl)-1-(2-ethoxycarbonylethyl)-1H-pyrazolo [3,4-b]pyridine Compound E: 1-(acetoxyethyl)-3-(3,5-di-tertiary butyl-4-hydroxyphenyl)-1H-pyrazolo[3,4-b]pyridine Pharmacological experiment 1

Analgesic Activity

The experiment was performed according to the method of Hendershot et al described in J. Pharmacol. Exp. Ther., vol. 125, P. 237 (1959). Male ddY mice weighing 18-25 g were used in groups of 6-18. One hour after the oral administration of test compound solution (10 ml/kg), 10 ml/kg of 0.02% aqueous phenylquinone solution was intraperitoneally administered to the animal. The frequency of stretch symptom thus induced measured for 20 minutes. The inhibitory rate was determined in comparison with the control group and the 50% effective dose ($ED_{50}$, mg/kg) was caluculated according to the linear regression method.

Pharmacological experiment 2

Effect on Acute Inflammation

The experiment was performed according to the method of Winter et al described in Proc. Soc. Exp. Biol. Med., vol. 111, p. 544 (1962). Male Donryu rats weighing about 140 g which was fastened for 18 hours were used in groups of five animals. Test compound solution was orally administered and one hour later, 0.05 ml of saline solution containing 1% carrageenin was injected into the right hind paw. Three hours later, the foot volume was measured by the water displacement method. The rate of increase against the foot volume before the injection of carrageenin was calculated, and the inhibitory rate was determined as compared with the control group. The 50% effective dose ($ED_{50}$, mg/kg) was determined by the linear regression method.

Pharmacological experiment 3

Effect on Chronic Inflammation

The experiment was performed by employing 10-week old male Lewis rats according to the method of Newbould described in Brit. J. Pharmacol., vol. 21, p. 127 (1963). Dead tubercle bacilli ($R_{35}H_5$ type) suspended in liquid paraffin (0.5 mg/0.1 ml) was inoculated as adjuvant into the skin at the base of tail. Animals with arthritis were chosen on the 15th day and divided into groups of seven. Test compound solution (5 ml/kg) was orally administered once a day from 15th day of 24th day consecutively. The rate of change of the foot volume on the 24th day against the foot volume on the 15th day was calculated, and the inhibitory rate was determined as compared with the control group. The minimun effective dose (MED, mg/kg) was obtained based on the dose indicating the decrease of foot volume than the foot volume on the 15th day.

Pharmacological experiment 3

Effect on the Platelet Aggregation induced by Arachidonic Acid

Male Hartley guinea pigs weighing 400-500 g were subjected to the abdominal operation under etherization. The citrated blood (9 volumes of blood and one volume of 3.8% sodium citrate solution) was collected from the abdominal aorta. Immediately, the blood was centrifuged at 150×g for 3 minutes to obtained platelet-rich plasma (PRP) as a supernatant. The remaining blood was centrifuged at 1400×g for 10 minutes to obtain platelet-poor plasma (PPP) as a supernatant. The number of platelet in PRP was adjusted to $4-6\times10^5$ platelets/mm$^3$ by adding PPP thereto The platelet aggregation was measured by using a platelet aggregometer according to the method of Born et al described in J. Physiol., vol. 168, p. 178 (1963). Test compound solution was added to PRP under stirring at 1500 rpm at 37°

C., and two minutes later arachidonic acid (final concentration: $5 \times 10^{-4}$M) is added thereto. The change of transmittance was recorded consecutively. The transmittance was adjusted to 0 and 100% with PRP and PPP, respectively. The inhibitory rate was calculated against the control group by using the maximum aggregation value as an index, and 50% inhibitory concentration($IC_{50}$, μg/ml) was determined by the linear regression method.

Results: The results of the above experiments are sammerized in the following Table.

TABLE 1

| Test Compound | Pharmacological Experiment | | | |
|---|---|---|---|---|
| | (1) $ED_{50}$ (mg/kg, p.o.) | (2) $ED_{50}$ (mg/kg, p.o.) | (3) MED (mg/kg, p.o.) | (4) $IC_{50}$ (g/ml) |
| Compound A | 9.5 | 70 | 0.3 | 1.05 |
| Compound B | 19 | 44 | 3 | 0.09 |
| Compound C | 1.1 | 8.0 | 0.3 | 0.95 |
| Compound D | 0.56 | 8.3 | 1 | 0.12 |
| Compound E | 0.35 | 14 | 0.3 | 0.90 |

Experiment on Acute Toxicity

The 50% lethal dose ($LD_{50}$, mg/kg) of Test Compounds A–E by the intraperitoneal administration to mice was about 300 mg/kg or more, and $LD_{50}$ value of these compounds by the oral administration was about 1000 mg/kg or more.

FORMULATION EXAMPLE 1

To a mixture of 50 g of the compound of the present invention, 45 g of lactose, 20 g of corn starch and 7 g of light, anhydrous silicic acid was added a solution of 1 g of hydroxypropyl cellulose in 20 ml of water, and kneaded well. The obtained mixture was granulated and dried. To the granule thus obtained were added 16.5 g of crystalline cellulose and 0.5 g of magnesium stearate, and mixed and then punched into the tablets weighing 140 mg each.

FORMULATION EXAMPLE 2

To 1.9 g of the melted WITEPSOL (Registered Trade Mark) W-35 with keeping at 38°–40° C. was added 0.1 g of the compound of the present invention, and dispersed homogeneously. The dispersion under warming was filled up in a container to obtain suppositories.

The present invention will be explained by the following reference examples and preparative examples in more detail, but these examples are not to be construed as limiting the present invention.

REFERENCE EXAMPLE 1

To a solution of 282 g of 2-chloronicotinoyl chloride and 400 g of 2,6-di-tertiary butylphenol in 1000 ml of dichloroethane under ice-cooling is added dropwise a solution of 500 g of anhydrous stannic chloride in 250 ml of dichloroethane with stirring over 50 minutes. The reaction temperature is kept below 5° C. during the addition. After completion of the addition, the mixture is stirred at room temperature for 1.5 hours. The resulting reaction mixture is poured into ice-cold water and stirred for a while. The organic layer is separated, washed with water, dried and then concentrated. The obtained residue is recrystallized from an aqueous solution of 80% methanol to give 442 g of 4-(2-chloronicotinoyl)-2,6-di-tertiary butylphenol as pale yellow crystals, melting at 135°–137° C.

REFERENCE EXAMPLE 2

The similar procedure in reference example 1 by using 19 g of 2-chloro-6-methylnicotinoyl chloride, 24.7 g of 2,6-di-tertiary butylphenol and 31.3 g of anhydrous stannic chloride is performed and the obtained crude product is recrystallized from hexane to give 29.8 g of 4-(2-chloro-6-methylnicotinoyl)-2,6-di-tertiary butylphenol as pale yellow crystals, melting at 116°–117° C.

REFERENCE EXAMPLE 3

The similar procedure in reference example 1 by using 12.2 g of 2-chloro-4,6-dimethylnicotinoyl chloride, 14.8 g of 2,6-di-tertiary butylphenol and 18.8 g of anhydrous stannic chloride in dichloroethane is performed and the obtained crude product is recrystallized from hexane to give 18.3 g of 4-(2-chloro-4,6-dimethylnicotinoyl)-2,6-di-tertiary butylphenol as pale yellow crystals, melting at 129°–132° C. According to the similar manner as the above Reference Examples, 4-(2-chloro-6-isopropylnicotinoyl)-2,6-di-tertiary butylphenol, melting at 109°–110° C. is prepared.

EXAMPLE 1

A solution of 69.1 g of 4-(2-chloronicotinoyl)-2,6-di-tertiary butylphenol and 45 g of hydrazine hydrate in 380 ml of pyridine is refluxed for 5 hours. After the pyridine is distilled off under reduced pressure, to the obtained residue is added water. The crude crystals precipitated are recrystallized from ethanol to give 62.5 g of 3-(3,5-di-tertiary butyl-4-hydroxyphenyl)-1H-pyrazolo[3,4-b]pyridine as white crystals, melting at 216°–217° C.

EXAMPLE 2

The similar procedures in Example 1 by using 15.5 g of 4-(2-chloro-6-methylnicotinoyl)-2,6-di-tertiary butylphenol, 9.7 g of hydrazine hydrate and 85 ml of pyridine are carried out, and then the obtained crude crystals are recrystallized from ethanol to give 11.8 g of 3-(3,5-di-tertiary butyl-4-hydroxyphenyl)-6-methyl-1H-pyrazolo[3,4-b]pyridine as white crystals, melting at 239°–240° C.

EXAMPLE 3

A mixture of 18.3 g of 4-(2-chloro-4,6-dimethylnicotinoyl)-2,6-di-tertiary butylphenol, 11 g of hydrazine hydrate and 100 ml of pyridine is reacted and the product is treated in a similar manner as Example 1 to give 15.5 g of 3-(3,5-di-tertiary butyl-4-hydroxyphenyl)-4,6-dimethyl-1H-pyrazolo[3,4-b]pyridine as white crystals, melting at 257°–258° C.

EXAMPLE 4

A solution of 4-(2-chloro-6-isopropylnicotinoyl)-2,6-di-tertiary butylphenol and hydrazine hydrate in pyridine is refluxed. After the pyridine is distilled off, to the residue is added water. The resulting crystals are recrystallized from ethanol to give 3-(3,5-di-tertiary butyl-4-hydroxyphenyl)-6-isopropyl-1H-pyrazolo[3,4-b]pyridine.

EXAMPLE 5

A mixture of 30 g of 4-(2-chloronicotinoyl)-2,6-di-tertiary butylphenol, 15 g of methylhydrazine and 150 ml of pyridine is reacted and treated in a similar manner as Example 1, and the obtained crude crystals are recrystallized from ethanol to give 27.3 g of 3-(3,5-di-tertiary butyl-4-hydroxyphenyl)-1-methyl-1H-pyrazolo[3,4-b]pyridine as white crystals, melting at 152°–154° C.

EXAMPLE 6

A solution of 7 g of 4-(2-chloronicotinoyl)-2,6-di-tertiary butylphenol and 2.4 g of phenylhydrazine in 40 ml of pyridine is refluxed for 7 hours. After the pyridine is distilled off under reduced pressure, to the residue is added water and the precipitated crystals are washed with water to give crude crystals of 4-(2-chloronicotinoyl)-2,6-di-tertiary butylphenol phenylhydrazone, melting at 181° C. with decomposition in an almost quantitative amount.

The crude product is suspended into 80 ml of isopentyl alcohol followed by adding 5 g of potassium carbonate thereto, and the mixture is refluxed for 7 hours. After the isopentyl alcohol is distilled off under reduced pressure and water is added to the residue, the precipitate is extracted with toluene, and the extract is washed with water, dried and then concentrated. Recrystallization of the residue from ethanol gives 6.5 g of 3-(3,5-di-tertiary butyl-4-hydroxyphenyl)-1-phenyl-1H-pyrazolo[3,4-b]pyridine as pale green crystals, melting at 174°–175° C.

EXAMPLE 7

A mixture of 1.8 g of 4-(2-chloro-6-methylnicotinoyl)-2,6-di-tertiary butylphenol and 0.7 g of methylhydrazine is reacted in a similar manner as Example 1 and the resulting product is recrystallized from ethanol to give 1.6 g of 3-(3,5-di-tertiary butyl-4-hydroxyphenyl)-1,6-dimethyl-1H-pyrazolo[3,4-b]pyridine as white crystals, melting at 178°–181° C.

EXAMPLE 8

By the use of 1.8 g of 4-(2-chloro-6-methylnicotinoyl)-2,6-di-tertiary butylphenol and 2-hydrazinoethanol, the reaction is similarly carried out as Example 1 and recrystallization from ethanol gives 3-(3,5-di-tertiary butyl-4-hydroxyphenyl)-1-(2-hydroxyethyl)-6-methyl-1H-pyrazolo[3,4-b]-pyridine as white crystals, melting at 183°–185° C.

EXAMPLE 9

To a solution of 6.5 g of 3-(3,5-di-tertiary butyl-4-hydroxyphenyl)-1H-pyrazolo 3,4-b pyridine, which can be prepared by the procedures in Example 1, in 50 ml of dimethylformamide are added 3.6 g of potassium carbonate and then 4 g of ethyl iodide. After stirring at 60° C. for 6.5 hours, the resulting mixture is poured into ice-cold water and the precipitate is extracted with toluene. The extract is washed with water, dried and concentrated, and then the resulting residue is recrystallized from hexane to give 5.6 g of 3-(3,5-di-tertiary butyl-4-hydroxyphenyl)-1-ethyl-1H-pyrazolo 3,4-b pyridine as pale pink crystals melting at 124°–126° C.

EXAMPLE 10

3-(3,5-Di-tertiary butyl-4-hydroxyphenyl)-1-propyl-1H-pyrazolo[3,4-b]pyridine, melting at 97°–98° C. is prepared by reacting the compound of Example 1 with propyl bromide in a similar manner as Example 9, and recrystallizing from hexane.

EXAMPLE 11

3-(3,5-Di-tertiary butyl-4-hydroxyphenyl)-1-isopropyl-1H-pyrazolo[3,4-b]pyridine, melting at 147° C. is prepared by reacting the compound of Example 1 with isopropyl bromide similarly in Example 9, and recrystallizing from isopropyl ether.

EXAMPLE 12

1-Butyl-3-(3,5-di-tertiary butyl-4-hydroxyphenyl)-1H-pyrazolo[3,4-b]pyridine, melting at 94°–96° C. is prepared by reacting the compound of Example 1 with butyl bromide similarly in Example 9, and recrystallizing from petroleum ether.

EXAMPLE 13

3-(3,5-Di-tertiary butyl-4-hydroxyphenyl)-1-octyl-1H-pyrazolo[3,4-b]pyridine is prepared by reacting the compound of Example 1 with octyl iodide as yellowish brown oil in a similar manner as Example 9.

Nuclear Magnetic Resonance (Deutero choloroform):

4.62 ppm, 2.04 ppm, 0.9 ppm.

EXAMPLE 14

3-(3,5-Di-tertiary butyl-4-hydroxyphenyl)-1-(3-chloropropyl)-1H-pyrazolo[3,4-b]pyridine, melting at 107°–109° C. is prepared by reacting the compound of Example 1 with 3-chloropropyl bromide in a similar manner as Example 9, and recrystallizing from acetonitrile.

EXAMPLE 15

1-Allyl-3-(3,5-di-tertiary butyl-4-hydroxyphenyl)-1H-pyrazolo[3,4-b]pyridine, melting at 120°–123° C. is obtained by reacting the compound by Example 1 with allyl chloride in a similar manner as Example 9, and recrystallizing from hexane.

EXAMPLE 16

3-(3,5-Di-tertiary butyl-4-hydroxyphenyl)-1-(2-propynyl)-1H-pyrazolo[3,4-b]pyridine, melting at 172°–174° C. is obtained by reacting the compound of Example 1 with 2-propynl chloride in a similar manner as Example 9, and recrystallizing from ethanol.

EXAMPLE 17

1-Benzyl-3-(3,5-di-tertiary butyl-4-hydroxyphenyl)-1H-pyrazolo[3,4-b]pyridine, melting at 155°–157° C. is obtained by reacting the compound of Example 1 with benzyl chloride in a similar manner as Example 9, and recrystallizing from ethanol.

EXAMPLE 18

3-(3,5-Di-tertiary butyl-4-hydroxyphenyl)-1-(4-chlorobenzyl)-1H-pyrazolo[3,4,-b]pyridine, melting at 163°–164° C. is obtained by reacting the compound of Example 1 with 4-chlorobenzyl chloride in a similar manner as Example 9, and recrystallizing from ethanol.

EXAMPLE 19

3-(3,5-Di-tertiary butyl-4-hydroxyphenyl)-1-(4-methylbenzyl)-1H-pyrazolo[3,4-b]pyridine, melting at 134°–135° C. is obtained by reacting the compound of Example 1 with 4-methylbenzyl chloride in a similar manner as Example 9, and recrystallizing from isopropyl ether.

EXAMPLE 20

3-(3,5-Di-tertiary butyl-4-hydroxyphenyl)-1-(3-trifluoromethylbenzyl)-1H-pyrazolo[3,4-b]pyridine, melting at 160°–163° C. is obtained by reacting the compound of Example 1 with 3-trifluoromethylbenzyl chloride in a similar manner as Example 9, and recrystallizing from isopropyl alcohol.

EXAMPLE 21

3-(3,5-Di-tertiary butyl-4-hydroxyphenyl)-1-(4-nitrobenzyl)-1H-pyrazolo[3,4-b]pyridine, melting at 143°–145° C. is obtained by reacting the compound of Example 1 with 4-nitrobenzyl chloride in a similar manner as Example 9, and then recrystallizing from isopropyl ether.

EXAMPLE 22

3-(3,5-Di-tertiary butyl-4-hydroxyphenyl)-1-(2-thenyl)-1H-pyrazolo[3,4-b]pyridine, melting at 138°–141° C. is obtained by reacting the compound of Example 1 with 2-thenyl chloride in a similar manner, and then recrystallizing from hexane.

EXAMPLE 23

3-(3,5-Di-tertiary butyl-4-hydroxyphenyl)-1-(4-methoxybenzyl)-1H-pyrazolo [3,4-b] pyridine is obtained by reacting the compound of Example 1 with 4-methoxybenzyl chloride in a similar manner as Example 9.

EXAMPLE 24

3-(3,5-Di-tertiary butyl-4-hydroxyphenyl)-1-(3-pyridylmethyl)-1H-pyrazolo [3,4-b] pyridine as a pale brown oil is obtained by reacting the compound of Example 1 with 3-pyridylmethyl chloride in a similar manner as Example 9.

Nuclear Magnetic Resonance (Deutero chloroform): 1.52 ppm, 5.76 ppm.

EXAMPLE 25

3-(3,5-Di-tertiary butyl-4-hydroxyphenyl)-1-cyclopropylmethyl-1H-pyrazolo[3,4-b]pyridine, melting at 135°–137° C. is obtained by reacting the compound of Example 1 with cyclopropylmethyl p-toluenesulfonate in a similar manner as Example 9, and then recrystallizing from isopropyl ether.

EXAMPLE 26

3-(3,5-Di-tertiary butyl-4-hydroxyphenyl)-1-(2,2,3,3-tetrafluoropropyl)-1H-pyrazolo[3,4-b]pyridine, melting at 105°–106° C. is obtained by reacting the compound of Example 1 with 2,2,3,3-tetrafluoropropyl p-toluenesulfonate in a similar manner as Example 9, and then recrystallizing from 70% aqueous ethanol.

EXAMPLE 27

3-(3,5-Di-tertiary butyl-4-hydroxyphenyl)-1-(2,2,2-trifluoroethyl)-1H-pyrazolo[3,4-b]pyridine, melting at 104.5°–105.5° C. is obtained by reacting the compound of Example 1 with 2,2,2-trifluoroethyl p-toluenesulfonate in a similar manner as Example 9, and then recrystallizing from hexane.

EXAMPLE 28

3-(3,5-Di-tertiary butyl-4-hydroxyphenyl)-1-(2-dimethylaminoethyl)-1H-pyrazolo[3,4-b]pyridine dihydrochloride, melting at 145°–147° C. is obtained by reacting the compound of Example 1 with 2-dimethylaminoethyl chloride in a similar manner as Example 9, converting thus obtained oil into the hydrochloride and then recrystallizing a mixed solvent of ethyl acetate and ethanol.

EXAMPLE 29

3-(3,5-Di-tertiary butyl-4-hydroxyphenyl)-1-(3-dimethylaminopropyl)-1H-pyrazolo[3,4-b]pyridine dihydrochloride, melting at 204°–205° C. is obtained by reacting the compound of Example 1 with 3-dimethylaminopropyl chloride in a similar manner as Example 9, converting thus obtained oil into the hydrochloride and then recrystallizing from a mixed solvent of ethyl acetate and ethanol.

EXAMPLE 30

3-(3,5-Di-tertiary butyl-4-hydroxyphenyl)-1-(2-morpholinoethyl)-1H-pyrazolo[3,4-b]pyridine, melting at 187°–188° C. is obtained by reacting the compound of Example 1 with 2-morpholinoethyl chloride in a similar manner as Example 9, and then recrystallizing from acetonitrile.

EXAMPLE 31

3-(3,5-Di-tertiary butyl-4-hydroxyphenyl)-1-(2-piperidinoethyl)-1H-pyrazolo[3,4,-b]pyridine, melting at 109°–112° C. is obtained by reacting the compound of Example 1 with 2-piperidinoethyl chloride in a similar manner as Example 9, and then recrystallizing from acetonitrile.

EXAMPLE 32

3-(3,5-Di-tertiary butyl-4-hydroxyphenyl)-1-[2-(2-oxo-1-pyrrolidinyl)ethyl]-1H-pyrazolo[3,4-b]pyridine, melting at 148°–150° C. is obtained by reacting the compound of Example 1 with 1-(2-chloroethyl)-2-pyrrolidone in a similar manner as Example 9, and then recrystallizing from isopropyl ether.

EXAMPLE 33

3-(3,5-Di-tertiary butyl-4-hydroxyphenyl)-1-(2-methylthioethyl)-1H-pyrazolo[3,4-b]pyridine, melting at 104°–106° C. is obtained by reacting the compound of Example 1 with 2-methylthioethyl chloride in a similar manner as Example 9, and then recrystallizing from isopropyl alcohol.

EXAMPLE 34

3-(3,5-Di-tertiary butyl-4-hydroxyphenyl)-1-(2-oxotetrahydrofuran-3-yl)-1H-pyrazolo[3,4-b-]pyridine, melting at 164°–167° C. is obtained by reacting the compound of Example 1 with 3-bromo-tetrahydro-2-furanone in a similar manner as Example 9, and then recrystallizing from isopropyl ether.

EXAMPLE 35

3-(3,5-Di-tertiary butyl-4-hydroxyphenyl)-1-ethoxycarbonylmethyl-1H-pyrazolo[3,4-b]pyridine, melting at 117°–120° C. is obtained by reacting the compound of Example 1 with ethyl chloroacetate in a similar manner as Example 9, and then recrystallizing from isopropyl ether.

EXAMPLE 36

3-(3,5-Di-tertiary butyl-4-hydroxyphenyl)-1-(2-ethoxycarbonylethyl)-1H-pyrazolo[3,4-b]pyridine, melting at 105°–106° C. is obtained by reacting the compound of Example 1 with ethyl 3-bromopropionate in a similar manner as Example 9, and then recrystallizing from isopropyl ether.

EXAMPLE 37

3-(3,5-Di-tertiary butyl-4-hydroxyphenyl)-1-carbamoylmethyl-1H-pyrazolo[3,4-b]pyridine, melting at 162°–164° C. is obtained by reacting the compound of Example 1 with 2-chloroacetamide in a similar manner as Example 9, and then recrystallizing from acetonitrile.

EXAMPLE 38

3-(3,5-Di-tertiary butyl-4-hydroxyphenyl)-1-(1-carbamoylethyl)-1H-pyrazolo[3,4-b]pyridine, melting at 192°–194° C. is obtained by reacting the compound of Example 1 with 2-bromopropionamide in a similar manner as Example 9, and then recrystallizing from toluene.

EXAMPLE 39

3-(3,5-Di-tertiary butyl-4-hydroxyphenyl)-1-(2-carbamoylethyl)-1H-pyrazolo[3,4-b]pyridine, melting at 154°–157° C. is obtained by reacting the compound of Example 1 with 3-chloropropionamide in a similar manner as Example 9, and then recrystallizing from a mixed solvent of toluene and hexane.

EXAMPLE 40

3-(3,5-Di-tertiary butyl-4-hydroxyphenyl)-1-(2-oxo-1-pyrrolidinylcarbonyl)methyl-1H-pyrazolo[3,4-b]pyridine as a yellowish brown amorphism is obtained by reacting the compound of Example 1 with 1-chloroacetyl-2-pyrrolidone.

Nuclear Magnetic Resonance (Deutero chloroform): 5.90 ppm, 3.82 ppm, 2.66 ppm, 2.10 ppm.

EXAMPLE 41

3-(3,5-Di-tertiary butyl-4-hydroxyphenyl)-1-cyanomethyl 1H-pyrazolo[3,4-b]pyridine, melting at 141°–143° C. is obtained by reacting the compound of Example 1 with chloroacetonitrile in a similar manner as Example 9, and then recrystallizing from a mixed solvent with hexane and ethanol.

EXAMPLE 42

3-(3,5-Di-tertiary butyl-4-hydroxyphenyl)-1-(2-cyanoethyl)-1H-pyrazolo[3,4-b]pyridine, melting at 158°–160° C. is obtained by reacting the compound of Example 1 with 3-chloropropionitrile in a similar manner as Example 9, and then recrystallizing from isopropyl alcohol.

EXAMPLE 43

(i) To a solution of 5 g of 3-(3,5-di-tertiary butyl-4-hydroxyphenyl)-1H-pyrazolo[3,4-b]pyridine in 40 ml of dimethylformamide are added 2.5 g of 2-bromoethanol and 2.8 g of potassium carbonate. After stirring at 65° C. for 12 hours, the resulting mixture is poured into ice-cold water and the precipitate is extracted with ethyl acetate. The ethyl acetate layer is washed with water, dried and then concentrated. The residue is recrystallized from a mixed solvent of hexane and toluene to give 4.6 g of 3-(3,5-di-tertiary butyl-4-hydroxyphenyl)-1-(2-hydroxyethyl)-1H-pyrazolo[3,4-b]pyridine as pale yellow crystals, melting at 135°–137° C.

(ii) A solution of 45.2 g of 4-(2-chloronicotinoyl)2,6-di-tertiary butylphenol and 21 g of 2-hydrazinoethanol in 230 ml of pyridine is refluxed under stirring for 18 hours. After completion of the reaction, the pyridine is concentrated and 140 ml of ethanol and 70 ml of water are added to the residue. The mixture is warmed to dissolve and then cooled to 0° C. The precipitated crystals are collected by filtration, recrystallized from 70% dioxane and then dried to give 40 g of 3-(3,5-di-tertiary butyl-4-hydroxyphenyl)-1-(2-hydroxyethyl)-1H-pyrazolo[3,4-b]pyridine, melting at 135°–137° C.

EXAMPLE 44

3-(3,5-Di-tertiary butyl-4-hydroxyphenyl)-1-(3-hydroxypropyl)-1H-pyrazolo[3,4-b]pyridine, melting at 143°–144° C. is obtained by reacting the compound of Example 1 with 3-chloropropanol in a similar manner as Example 43, and then recrystallizing from isopropyl alcohol.

EXAMPLE 45

3-(3,5-Di-tertiary butyl-4-hydroxyphenyl)-1-(2-hydroxypropyl)-1H-pyrazolo[3,4-b]pyridine as yellowish brown amorphism is obtained by reacting the compound of Example 1 with 1-chloro-2-propanol in a similar manner as Example 43.

Nuclear Magnetic Resonance (Deutero dimethylsulfoxide): 4.29 ppm, 4.1–4.7 ppm, 1.16 ppm.

EXAMPLE 46

3-(3,5-Di-tertiary butyl-4-hydroxyphenyl)-1-(2,3-dihydroxypropyl)-1H-pyrazolo[3,4-b]pyridine as pale yellowish green amorphism is obtained by reacting the compound of Example 1 with 1-chloro-2,3-propanediol in a similar manner as Example 43.

Nuclear Magnetic Resonance (Deutero chloroform): 4.73 ppm, 4.21 ppm, 3.59 ppm.

EXAMPLE 47

To a solution of 7.8 g of 3-(3,5-di-tertiary butyl-4-hydroxyphenyl)-1H-pyrazolo[3,4-b]pyridine in 40 ml of dimethylformamide are added 4.9 g of potassium carbonate and 7.2 g of 2-methoxyethyl p-toluenesulfonate, and the mixture is stirred at 60° C. for 7 hours. The resulting mixture is poured into ice-cold water and the precipitate is extracted with toluene. The extract is washed with water, dried and concentrated. The residue is recrystallized from hexane to give 7.2 g of 3-(3,5-di-tertiary butyl-4-hydroxyphenyl)-1-(2-methoxyethyl)-1H-pyrazolo[3,4-b]pyridine as white crystals, melting at 111°–113° C.

EXAMPLE 48

3-(3,5-Di-tertiary butyl-4-hydroxyphenyl)-1-(2-ethoxyethyl)-1H-pyrazolo[3,4-b]pyridine (7.6 g), melting at 86°–88° C. is obtained by reacting 8.1 g of 3-(3,5-di-tertiary butyl-4-hydroxyphenyl)-1H-pyrazolo[3,4-b]pyridine with 9.2 g of 2-ethoxyethyl p-toluenesulfonate in a similar manner as Example 47, and then recrystallizing the obtained crude product from hexane.

EXAMPLE 49

3-(3,5-Di-tertiary butyl-4-hydroxyphenyl)-1-methoxymethyl-1H-pyrazolo[3,4-b]pyridine (4.2 g) as white crystals, melting at 113°–115° C. is obtained by reacting 4.8 g of 3-(3,5-di-tertiary butyl-4-hydroxyphenyl)-1H-pyrazolo[3,4-b]pyridine and 1,8 g of chloromethyl methyl ether in a similar manner as Example 9, and then recrystallizing the obtained crude product from hexane.

EXAMPLE 50

3-(3,5-Di-tertiary butyl-4-hydroxyphenyl)-1-(2-methoxyethyl)-6-methyl-1H-pyrazolo3,4-b]pyridine, melting at 132°–13° C. is obtained by reacting the compound of Example 2 with 2-methoxyethyl p-toluenesulfonate, and then recrystallizing from hexane.

EXAMPLE 51

(i) To a solution of 40 g of 3-(3,5-di-tertiary butyl-4-hydroxyphenyl)-1H-pyrazolo[3,4-b]pyridine in 300 ml of dimethylformamide are added 34,2 g of potassium carbonate and 31 g of 2-acetoxyethyl bromide, and the mixture is stirred at 60° C. for 11 hours. The resulting mixture is poured into ice-cold water and the precipitate is extracted with ethyl acetate and then the extract is washed with water, dried and concentrated. The resulting residue is recrystallized from isopropyl alcohol to give 43 g of 1-(2-acetoxyethyl)-3-(3,5-di-tertiary butyl-4-hydroxyphenyl)-1H-pyrazolo[3,4-b]pyridine as white crystals, melting at 115°–116° C.

(ii) To a solution of 5.2 g of the compound of Example 43 in 30 ml of chloroform is added 2.1 g of triethylamine, and the mixture is cooled and then stirred. To the reaction mixture is added dropwise 1.7 g of acetyl chloride below 0° C. over 5 minutes. After completion of the addition, the mixture is stirred at room temperature for 3 hours, and the reaction solution is washed with water, dried and concentrated. The residue is recrystallized from isopropyl alcohol to give 5 g of 1-(2-acetoxyethyl)-3-(3,5-di-tertiary butyl-4-hydroxyphenyl)-1H-pyrazolo[3,4-b]pyridine as white crystals, melting at 115°–116° C.

(iii) To a solution of 40 g of the compound of Example 43 in 320 ml of toluene is added 22 g of acetic anhydride under stirring, and refluxed for 8 hours. After completion of the reaction, the reaction mixture is cooled to 20° C., washed with 300 ml of water twice and dried over anhydrous sodium sulfate. The toluene is concentrated and the residue is recrystallized from ethanol and dried to give 37 g of 1-(2-acetoxyethyl)-3-(3,5-di-tertiary butylphenyl)-1H-pyrazolo[3,4-b]pyridine, melting at 115°–116° C.

EXAMPLE 52

(i) 1-(3-Acetoxypropyl)-3-(3,5-di-tertiary butyl-4-hydroxyphenyl)-1H-pyrazolo[3,4-b]pyridine (6.3 g) as white crystals, melting at 75°–77° C. is obtained by reacting 6.5 g of -(3,5-di-tertiary butyl-4-hydroxyphenyl)-1H-pyrazolo[3,4-b]pyridine with 4.1 g of 3-acetoxypropyl chloride in a similar manner as Example 51 (i), and recrystallizing the resulting crude product from hexane.

(ii) The same compound as above (i) (3.8 g), melting at 75°–77° C. is obtained by reacting 3.8 g of the compound of Example 44 with 0.95 g of acetyl chloride in a similar manner as Example 51 (ii), and recrystallizing the resulting.

EXAMPLE 53

To a solution of 4.2 g of the compound of Example 43 in 40 ml of dichloroethane are added 1.4 g of triethylamine and 1.8 g of propionic anhydride at room temperature, and the mixture is stirred at 30°–35° C. for 8 hours. The resulting solution is washed with water, dried and concentrated, and then the obtained residue is recrystallized from hexane to give 3.9 g of 3-(3,5-di-tertiary butyl-4-hydroxyphenyl)-1-(2-propopmupxuetju;)-1H-pyrazolo[3,4-b]pyridine as white crystals, melting at 82°–83° C.

EXAMPLE 54

3-(3,5-Di-tertiary butyl-4-hydroxyphenyl)-1-(2-propopmu;pxuetju;)-6-methyl-1H-pyrazolo[3,4-b]pyridine is obtained by reacting the compound of Example 8 with propionic anhydride in a similar manner as Example 53 and then recrystallizing from hexane.

EXAMPLE 55

To a solution of 3.7 g of the compound of Example 43 in 20 ml of chloroform is added 1.5 g of triethylamine, and to the mixture with stirring at −10°−−2° C. is added 1.4 g of ethyl chlorocarbonate dropwise. After completion of the addition, the whole mixture is stirred at 0° C. for 3 hours, and then at room temperature for 2 hours. The reaction solution is washed with water, dried and concentrated, and then the resulting residue is recrystallized from isopropyl ether to give 3.8 g of 3-(3,5-di-tertiary butyl-4-hydroxyphenyl)-1-(2-ethoxycarbonyloxyethyl)-1H-pyrazolo[3,4-b]-pyridine as white crystals, melting at 103°–105° C.

EXAMPLE 56

3-(3,5-Di-tertiary butyl-4-hydroxyphenyl)-1-(2-isobutyryloxyethyl)-1H-pyrazolo[3,4-b]pyridine, melting at 94°–96° C. is obtained by reacting the compound of Example 43 with isobutyryl chloride in a similar manner as Example 55 and recrystallizing from isopropyl ether.

EXAMPLE 57

3-(3,5-Di-tertiary butyl-4-hydroxyphenyl)-1-(2-pivaloyloxyethyl)-1H-pyrazolo[3,4-b]pyridine, melting at 85°–87° C. is obtained by reacting the compound of Example 43 with pivaloyl chloride in a similar manner as Example 55, and recrystallizing from hexane.

EXAMPLE 58

3-(3,5-Di-tertiary butyl-4-hydroxyphenyl)-1-(2-nicotinoyloxyethyl)-1H-pyrazolo[3,4-b]pyridine, melting at 134°–136° C. is obtained by reacting the compound of Example 43 with nicotinoyl chloride in a similar manner as Example 55, and recrystallizing from isopropyl ether.

EXAMPLE 59

3-(3,5-Di-tertiary butyl-4-hydroxyphenyl)-1-(2-dimethylcarbamoyloxyethyl)-1H-pyrazolo[3,4-b]pyridine, melting at 99°–101° C. is obtained by reacting the compound of Example 43 with dimethylcarbamyl chloride in a similar manner as Example 55, and recrystallizing from a mixed solvent of hexane and isopropyl ether.

EXAMPLE 60

3-(3,5-Di-tertiary butyl-4-hydroxyphenyl)-1-(2-ethoxycarbonyloxyethyl)-6-methyl-1H-pyrazolo[3,4-b]pyridine, melting at 145°–146° C. is obtained by reacting the compound of Example 8 with ethyl chlorocarbonate in a similar manner as Example 55, and recrystallizing from hexane.

EXAMPLE 61

To a solution of 6.8 g of the compound of Example 2 in 50 ml of dimethylformamide are added 4.1 g of potassium carbonate and 5 g of 2-bromoethyl acetate, and the mixture is stirred at 60° C. for 16.5 hours. The reaction mixture is poured into ice-cold water, and the precipitate is extracted with ethyl acetate. The extract is washed with water, dried and concentrated, and then the residue is recrystallized from hexane to give 5.9 g of 1-(2-acetoxyethyl)-3-(3,5-di-tertiary butyl-4-hydroxyphenyl)-6-methyl-1H-pyrazolo[-3,4-b]pyridine as pale yellowish green crystals, melting at 101.5°–103° C.

EXAMPLE 62

1-(Acetoxyethyl)-3-(3,5-di-tertiary butyl-4-hydroxyphenyl)-4,6-dimethyl-1H-pyrazolo[3,4-b]pyridine (6.1 g) as white crystals, melting at 110°–111° C. is obtained by reacting 7 g of the compound of Example 3 with 5 g of 2-bromoethyl acetate in a similar manner as Example 61 and then recrystallizing the resulting crude product from hexane.

EXAMPLE 63

(i) 3-(3,5-Di-tertiary butyl-4-hydroxyphenyl)-1-(2-hydroxyethyl)-6-isopropyl-1H-pyrazolo[3,4-b]pyridine as white crystals, melting at 110°–111° C. is obtained by reacting 4-(2-chloro-6-isopropylnicotinoyl)-2,6-di-tertiary butylphenol with 2-hydrazinoethanol in a similar manner as Example 1, and recrystallizing from isopropyl ether.

(ii) 1-(Acetoxyethyl)-3-(3,5-di-tertiary butyl-4-hydroxyphenyl)-6-isopropyl-1H-pyrazolo[3,4-b]pyridine as white crystals, melting at 121°–122° C. is obtained by reacting the thus obtained compound with acetyl chloride in a similar manner as Example 51 (ii), and then recrystallizing from hexane.

EXAMPLE 64

To a solution of 22 g of the compound of Example 35 in 150 ml of ethanol is added 135 ml of 1N aqueous sodium hydroxide solution, and the mixture is stirred at room temperature for an hour. After completion of the reaction, the mixture is acidified with dilute hydrochloric acid to precipitate crystals. The crude crystals are collected by filtration, washed with water and recrystallize from aqueous dioxane to give 17.8 g of 3-(3,5-ditertiary butyl-4-hydroxyphenyl)-1H-pyrazolo[3,4-b]pyridine-1-acetic acid as pale yellow crystals, melting at 210°–212° C.

EXAMPLE 65

3-[3-(3,5-Di-tertiary butyl-4-hydroxyphenyl)-1H-pyrazolo[3,4-b]pyridin-1-yl]propionic acid (5.2 g) as pale yellow crystals, melting at 183°–186° C. is obtained by treating 6.5 g of the compound of Example 36 in a similar manner as Example 64 and recrystallizing the resulting crude crystals from ethanol.

EXAMPLE 66

To a solution of 9.7 g of the compound of Example 1 in 70 ml of dimethylformamide are added 5.5 g of potassium carbonate and 6 g of ethyl 4-chlorobutyrate, and the mixture is stirred at 60° C. for 21 hours. The reaction mixture is poured into water and extracted with ethyl acetate. The extract is washed with water, dried and concentrated. To a solution of the residue in 100 ml of 80 % methanol is added 3 g of potassium hydroxide, and the mixture is stirred at room temperature for two hours. After completion of the reaction, the methanol is distilled off under reduced pressure and the residue is dissolved into water and the aqueous solution is acidified with dilute hydrochloric acid. The precipitated crystals are collected by filtration and then recrystalliz-ing from ethanol to give 8.3 g of 4-[3-(3,5-di-tertiary butyl-4-hydroxyphenyl)-1H-pyrazolo[3,4-b]pyridin-1-yl]butyric acid as pale yellow crystals, melting at 192°–194° C.

EXAMPLE 67

To a solution of 5.7 g of the compound of Example 64 in 40 ml of chloroform is added 1.8 g of triethylamine, and then to the mixture with stirring at −30° C. is added once 2 g of ethyl chlorocarbonate. After the whole mixture is stirred at −10° C. to −30° C. for 30 minutes, 1.3 g of diethylamine is added thereto. The reaction mixture is gradually warmed to room temperature with stirring for 2 hours. The resultant mixture is washed with water, dried and concentrated and then the obtained residue is recrystallized from acetonitrile to give 5.3 g of 2-[3-(3,5-di-tertiary butyl-4-hydroxyphenyl)-1H-pyrazolo[3,4-b]pyridin-1-ly]-N,N-diethylacetamide as pale yellow green crystals, melting at 187°–188° C.

EXAMPLE 68

3-(3,5-Di-tertiary butyl-4-hydroxyphenyl)-1-morpholinocarbonylmethyl-1H-pyrazolo[3,4-b]pyridine, melting at 207°–209° C. is obtained by reacting the compound of Example 64 with morpholine in a similar manner as Example 67, and recrystallizino from acetonitrile.

EXAMPLE 69

3-(3,5-Di-tertiary buty-4-hydroxyphenyl)-1-[4-(2-(hydroxyethyl)-1-piperazinyl]carbonylmethyl-1H-pyrazolo[3,4-b]pyridine, meltino at 240°–242° C. with decomoosition is obtained by reacting the compound of Example 64 with 4-(2-hydroxyethyl)piperazine in a similar manner as Example 67, and recrystallizing from ethanol.

EXAMPLE 70

To a solution of 6.5 g of the compound of Example 1 in 50 ml of chloroform and 2.4 g of triethylamine is added dropwise 1.9 g of acetyl chloride over 15 minutes under cooling and stirring. After addition, the resulting mixture is stirred under cooling for 2 hours and then at room temperature for 3 hours. The reaction solution is washed with water, dried and then concentrated. The obtained residue is recrystallized from ethanol to give 5.7 g of 1-acetyl-3-(3,5-di-tertiary butyl-4-hydroxyphenyl)-1H-pyrazolo[3,4-b]pyridine as oale yellow crvstals. melting at 169°–171° C.

EXAMPLE 71

3-(3,5-Di-tertiary butyl-4-hydroxyphenvl)-1-propionyl 1H-pyrazolo[3,4-b]pyridine, melting at 184°–185° C. is obtained by reacting the compound of Example 1 with propionyl chloride in a similar manner as Example 70, and recrystallizing from ethanol.

EXAMPLE 72

3-(3,5-Di-tertiary butyl-4-hydroxyphenyl)-1-hexanoyl-1H-pyrazolo[3,4-b]pyridine, melting at 112°–114° C. is obtained by reacting the compound of Example 1 with hexanoyl chloride in a similar manner as Example 70, and recrystallizing from hexane.

EXAMPLE 73

3-(3,5-Di-tertiary butyl-4-hydroxyphenyl)-1-(4-chlorobenzoyl)-1H-pyrazolo[3,4-b]pyridine, melting at 256°–258° C. is obtained by reacting the compound of Example 1 with 4-chlorobenzoyl chloride in a similar manner as Example 70, and recrystallizing from aqueous dioxane.

EXAMPLE 74

3-(3,5-Di-tertiary butyl-4-hydroxyphenyl)-1-(2-thenoyl)1H-pyrazolo[3,4-b]pyridine, melting at 240°–242° C. is obtained by reacting the compound of Example 1 with 2-thenoyl chloride in a similar manner as Example 70, amd recrystallizing from acetonitrile.

EXAMPLE 75

1-Acetoxyacetyl-3-(3,5-di-tertiary butyl-4-hydroxyphenyl)-1H-pyrazolo[3,4-b]pyridine, melting at 175°–177° C. is obtained by reacting the compound of Example 1 with acetoxyacetyl chloride in a similar manner as Example 70, and recrystallizing from isopropyl alcohol.

EXAMPLE 76

3-(3,5-Di-tertiary butyl-4-hydroxyphenyl)-1-ethoxycarbonyl-1H-pyrazolo[3,4-b]pyridine, melting at 161°–163° C. is obtained by reacting the compound of Example 1 with ethyl chlorocarbonate in a similar manner as Example 70, and recrystallizing from a mixed solvent of toluene and hexane.

EXAMPLE 77

3-(3,5-Di-tertiary butyl-4-hydroxyphenyl)-1-ethoxycarbonyl-6-methyl-1H-pyrazolo[3,4-b]pyridine, melting at 208°–209° C. is obtained by reacting the compound of Example 2 with ethyl chlorocarbonate in a similar manner as Example 70, and recrystallizing from ethanol.

EXAMPLE 78

(i) To a solution of 6.5 g of the compound of Example 1 in 50 ml of dimethylformamide are added 4.1 g of potassium carbonate and 4.1 g of 4-chloromethyl-2-oxo-1,3-dioxolane, and the mixture is stirred at 65° C. for 4 hours. After completion of the reaction, the reaction mixture is poured into ice-cold water, and the precipitate is extracted with ethyl acetate. The extract is washed with water, dried and concentrated, and then the obtained residue is recrystallized from isopropyl ether to give 6 g of 3-(3,5-di-tertiary butyl-4-hydroxyphenyl)-1-(2-oxo-1,3-dioxolan-4-ylmethyl)-1H-pyrazolo[3,4-b]pyridine as white crystals, melting at 140°–141° C.

(ii) To a solution of 4 g of the compound of Example 46 in 20 ml of pyridine with stirring under cooling is added 1.2 g of trichloromethyl chlorocarbonate dropwise over 15 minutes. After completion of the addition, the mixture is stirred at 5° C. for 30 minutes and then at room temperature for an hour. The reaction mixture is poured into ice-cold water and the precipitate is extracted with ethyl acetate. The extract is washed with water, dried and cencentrated, and the residue is recrystallized from isopropyl ether to give 3.6 g of the same compound as above (i), melting at 140°–141° C.

EXAMPLE 79

(i) By using 3.2 g of the compound of Example 1 and 1.6 g of 5-chloro-2-oxo-1,3-dioxane, the reaction is carried out in a similar manner as Example 78 (i) to give 3-(3,5-di-tertiary butyl-4-hydroxyphenyl)-1-(2-oxo-1,3-dioxan-5-yl)-1H-pyrazolo-[3,4-b]pyridine.

(ii) By using 4 g of 3-(3,5-di-tertiary butyl-4-hydroxyphenyl)-1-(1,3-dihydroxy-2-propyl)-1H-pyrazolo[3,4-b]pyridine and 1.2 g of trichloromethyl chlorocarbonate, the reaction is carried out in a similar manner as Example 78 (ii) to give the same compound as above (i).

EXAMPLE 80

To a solution 3.2 g of the compound of Example 1 in 20 ml of dimethylformamide are added 2 g of potassium carbonate and 1.6 g of 4-chloro-4-methyl-2-oxo-1,3-dioxolane, and the mixture is stirred at 60° C. for 6 hours. The reaction mixture is poured into ice-cold water and the precipitate is extracted with ethyl acetate. After the extract is washed with water, dried and concentrated, the residue is recrystallized from a mixed solvent of hexane and toluene to give 3 g of 3-(3,5-di-tertiary butyl-4-hydroxyphenyl)-1-(4-methyl-2-oxo-1,3-dioxolan-4-yl)-1H-pyrazolo[3,4-b]pyridine as white crystals, melting at 190°–191° C.

EXAMPLE 81

By using 3.8 g of the compound of Example 45 and 0.95 g of acetyl chloride, the reaction is carried out in a similar manner as Example 53 to give 1-(2-acetoxy-1-propyl)-3-(3,5-di-tertiary butyl-4-hydroxyphenyl)-1H-pyrazolo[3,4-b]pyridine.

EXAMPLE 82

3-(3,5-Di-tertiary butyl-4-hydroxyphenyl)-6-methyl-1-vinyl-1H-pyrazolo[3,4-b]pyridine, melting at 136°–137° C. is obtained according to the procedures described in above Examples.

Although the present invention has been adequately discussed in the foregoing specification and examples included therein, one readily recognizes that various changes and modifications may be made without departing from the spirit and scope thereof.

What is claimed is:

1. A pyrazolopyridine compound of the formula:

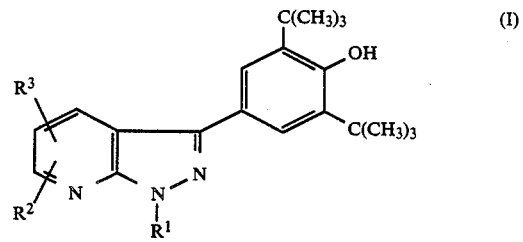

and a salt thereof, wherein $R^1$ is hydrogen; straight or branched chain alkyl having 1 to 20 carbon atoms; straight or branched chain alkenyl having 2 to 8 carbon atoms; straight or branched chain alkynyl having 2 to 8 carbon atoms; cycloalkyl having 3 to 7 carbon atoms; phenyl; substituted phenyl which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched alkyl having 1 to 8 carbon atoms which is substituted by at least one halogen; heteroaryl selected from the group consisting of furyl, thienyl, pyridyl, pyrazolyl, imidazolyl, pyrazinyl, benzimidazolyl, oxazolyl, thiazolyl and indolyl; substituted heteroaryl selected from the group consisting of furyl, thienyl, pyridyl, pyrazolyl, imidazolyl, pyrazinyl, benzimidazolyl, oxazolyl, thiazolyl and indolyl which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain haloalkyl having 1 to 8 carbon atoms in the heteroaromatic nucleus; straight or branched chain alkyl having 1 to 10 carbon atoms which is substituted by at least one halogen; hydroxyalkyl in which the alkyl moiety is a straight or branched chain alkyl having 1 to 8 carbon atoms; alkoxyalkyl in which the alkoxy moiety and the alkyl moiety each are straight or branched chains having 1 to 8 carbon atoms; acyloxyalkyl in which he acyl moiety is alkanoyl having 2 to 18 carbon atoms, benzoyl, substituted benzoyl which is substituted by at least one substituted selected from the group consisting of halogen, amino, nitro, hydroxy, straight or branched chain alkyl having 1 to 20 carbon atoms, straight or branched chain alkoxy having 1 to 10 carbon atoms and straight or branched chain haloalkyl having 1 to 8 carbon atoms on the benzene ring, heteroarylcarbonyl selected from the group consisting of furoyl, thenoyl, nicotinoyl, isonicotinoyl, pyrazolyl-carbonyl, imidazolylcarbonyl and benzimidazolylcarbonyl, or substituted heteroarylcarbonyl in which the heteroarylcarbonyl is selected from the group consisting of furoyl, thenoyl, nicotinoyl, isonicotinoyl, pyrazolylcarbonyl, imidazolylcarbonyl and benzimidazolylcarbonyl which is substituted by at least one subsituent selected from the group consisting of halogen, amino, nitro, hydroxy, straight or branched chain alkoxy having 1 to 10 carbon atoms and straight or branched chain haloalkl having 1 to 8 carbon atoms on the heteroaryl nucleus, and the alkyl moiety is straight or branched chain alkyl having 1 to 8 carbon atoms; carboxyalkyl in which the alkyl moiety is straight or branched chain alkyl having 1 to 8 carbon atoms; alkoxycarbonylalkyl in which the alkoxy moiety and the alkyl moiety each are straight or branched chains having 1 to 8 carbon atoms; cyanoalkyl in which the alkyl moiety is straight or branched chain alkyl having 1 to 8 carbon atoms; carbamoylalkyl in which the alkyl moiety is straight or branched chain alkyl having 1 to 8 carbon atoms; mono- or di-substituted carbamoylalkyl in which the substituent(s) to the nitrogen atom of the carbamoyl moiety is (are) selected from the group consisting of hydrogen, straight or branched chain alkyl having 1 to 8 carbon atoms, phenylalkyl in which the alkyl moiety is straight or branched chain alkyl having 1 to 8 carbon atoms, substituted phenylalkyl in which the alkyl moiety is straight or branched chain alkyl having 1 to 8 carbon atoms and which is substituted by at least one substituent selected from the group consisting of halogen, amino, nitro, hydroxy, straight or rbanched chain alkyl having 1 to 20 carbon atoms, straight or branched chain alkoxy having 1 to 10 carbon atoms and straight or branched chain haloalkyl having 1 to 8 carbon atoms on the phenyl nucleus, and heterocycle selected from the group consisting of 1-pyrrolidinyl, 2-oxo-1-pyrrolidinyl, and piperidino, to be formed together with the adjacnet nitrogen atom of the carbonoyl moiety and the alkyl moiety is the carbomoyl alkyl is straight or branched chain alkyl having 1 to 8 carbon atoms; alkoxycarbonyloxyalkyl in which the alkoxy moiety and the alkyl moiety each are straight or branched chains having 1 to 8 carbon atoms; carbamoxyalkyl in which the alkyl moiety is straight or branched chain alkyl having 1 to 8 carbon atoms; mono- or di-substituted carbamoyloxyalkyl in which the substitutent(s) to the nitrogen atom of the carbamoyl moiety is (are) selected from the group consisting of hydrogen, straight or branched chain alkyl having 1 to 8 carbon atoms, phenylalkyl in which the alkyl moiety is straight or branched chain alkyl having 1 to 8 carbon atoms, substituted phenylalkyl in which the alkyl moiety is straight or branched chain alkyl having 1 to 8 carbon atoms and which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain halozlkyl having 1 to 8 carbon atoms on the phenyl nucleus, and heterocycle selected from the group consisting of 1-pyrrolidinyl, 2-oxo-1-pyrrolidinyl, and piperidino, to be formed together with the adjacent nitrogen atom of the carbamoyl and the alkyl moiety in the carbanoylalkyl is straight or branched chain alkyl having 1 to 8 carbon atoms; alkylthiolkyl in which the alkylthio moiety and the alkyl moiety each are straight or branched chains having 1 to 8 carbon atoms; phenylalkyl in which the alkyl moiety is straight or branched chain alkyl having 1 to 8 carbon atoms; substituted phenylalkyl in which the alkyl moiety is straight or branched chain alkyl having 1 to 8 carbon atoms and which is substituted by at least one substituent selected from the group consisting of halogen, amino, nitro, hydroxy, straight or branched chain alkyl having 1 to 20 carbon atoms, straight or branched chain haloalkyl having 1 to 10 carbon atoms and straight or branched chain haloalkyl having 1 to 8 carbon atoms on the phenyl nucleus; heteroarylalkyl in which the heteroaryl moiety is selected from the group consisting of furyl, thienyl, pyridyl, pyrazolyl, imidazolyl, pyrazinyl, benzimidazolyl, oxazolyl, thiazolyl and indolyl and the alkyl moiety is straight or branched chain alkyl having 1 to 8 carbon atoms; substituted heteroarylalkyl in which the substituted heteroaryl moiety is selected from the group consisting of furyl, thienyl, pyridyl, pyrazolyl, imidazolyl, pyrazinyl, benzimidazolyl, oxazolyl, thiazolyl and indolyl which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain haloalkyl having 1 to 8 carbon a atoms on the heteroaryl nucleus, and the alkyl moiety is straight or branched chain alkyl having 1 to 8 carbon atoms; cycloalkylalkyl in which the cyloalkyl moiety is cyclic alkyl aaving 3 to 7 carbon atoms and the alkyl moiety is straight or branched chain alkyl having 1 to 8 carbon atoms; a group of the formula;

where each of $R_a$ and $R_b$ is hydrogen, straight or branched chain alkyl having 1 to 20 carbon atoms, phenylalkyl in which the alkyl moiety is straight or branched chain alkyl having 1 to 8 carbon atoms, substituted phenylalkyl in which the alkyl moiety is straight or branched chain alkyl having 1 to 8 carbon atoms and which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain halozlkyl having 1 to 8 carbon atoms on the phenyl nucleus, or $R_a$ and $R_b$ together with the adjacent nitrogen atom form a heterocycle selected from the group consisting of 1-pyrrolidinyl, 2-oxo-1-pyrrolidinyl, and piperidino, and n is an integer of 1 to 8; alkanoyl having 2 to 18 carbon atoms; alkoxycarbonyl in which the alkoxy moiety is alkoxy having 1 to 10 carbon atoms; acyloxyalkanoy in which the acyl moiety is alkanoyl having 2 to 18 carbon atoms, benzoyl, substituted benzoyl which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain haloalkyl having 1 to 8 carbon atoms on the benzene ring, heteroarylcarbonyl selected from the group consisting of furoyl, thenoyl, nicotinoyl, isonicotinoyl, pyrazolylcarbonyl, imidazolylcarbonyl and benzimidazolylcarbonyl, substituted heteroarylcarbonyl in which the heteroarylcarbonyl selected from the group consisting of furoyl, thenoyl, nicotinoyl, isonicotinoyl, pyrazolylcarbonyl, imidazolylcarbonyl and enzimidazolylcarbonyl which is substituted by at least one substituent selected from the group consisting of halogen, amino, nitro, hydroxy, straight or branched chain alkoxy having 1 to 10 carbon atoms and straight or branched chain haloalkyl having 1 to 8 carbon atoms on the heteroaryl nucleus, and the alkanoyl moiety is alkanoyl having 2 to 18 carbon atoms; benzoyl, substituted benzoyl which is substituted by at least one substituent selected from the group consisting of halogen, amino, nitro, hydroxy, straight or branched chain alkyl having 1 to 20 carbon atoms, straight or branched chain alkoxy having 1 to 10 carbon atoms and straight or branched chain haloalkyl having 1 to 8 carbon atoms on the benzene ring; heteroarylcarbonyl selected from the group consisting of furoyl, thenoyl, nicotinoyl, isonicotinoyl, pyrazolylcarbonyl, imidazolylcarbonyl and benzimidazolylcarbonyl; substituted heteroarylcarbonyl in which the heteroarylcarbonyl is selected from the group consisting of furoyl, thenoyl, nicotinoyl, isonicotinoyl, pyrazolylcarbonyl, imidazolylcarbonyl and benzimidazolylcarbonyl which is substituted by at least one substituent selected from the group consisting of halogen, amino, nitro, hydroxy, straight or branched chain alkoxy having 1 to 10 carbon atoms and straight or branched chain haloalkyl having 1 to 8 carbon atoms on the heteroaryl nucleus; or a group of the formula;

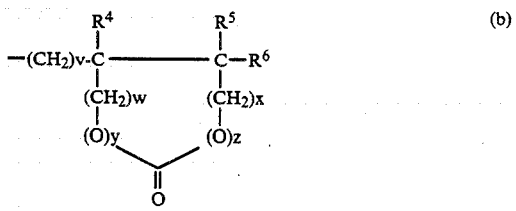

where each of $R^4$, $R^5$ and $R^6$ is hydrogen or straight or branched chain alkyl having 1 to 20 carbon atoms, or $R^4$ and one of $R^5$ or $R^6$ together form a single bond, and each of v, w, x, y and z is an integer of 0 and 1 to 4; and each of $R^2$ and $R^3$ is hydrogen, halogen, straight or branched chain alkyl having 1 to 20 carbon atoms, or straight or branched chain alkyl having 1 to 10 carbon atoms which is substituted by at least one halogen.

2. A pyrazolopyridine compound as claimed in claim 1, wherein said compound is selected from the group consisting of 1-(2-acetoxyethyl)-3-(3,5-di-tertiary butyl-4-hydroxyphenyl)-1H-pyrazolo[3,4-1H-pyrazolo[3,4-b]pyridine, 3-(3,5-di-tertiary butyl-4-hydroxy-phenyl)-1-(2-hyrdroxyethyl)-1H-pyrazolo[3,4 -b]-pyridine, 3-(3,5-di-tertiary butyl-4-hydroxphenyl)-1-methyl-1H-pyrazolo [3,4-b]pyridine, 3-(3,5-di-tertiary butyl-4-hydroxyphenyl)-1-(2-propionyloxyethyl)-1H-pyrazolo[3,4-b-]-pyridine, 3-(3,5-di-tertiary butyl-4-hydroxyphenyl)-1-(2-ethoxycarbonyloxyethyl)-1H-pyrazolo[3,4-b]pyridine, 1-(2-acetoxyethyl)-3-(3,5-di-tertiary butyl-4-hydroxyphenyl)-5-methyl-1H-pyrazolo[3,4-b]pyridine and 3-(3,5-di-tertiary butyl-4-hydroxyphenyl)-1-(2-dimethyl-aminoethyl)-1H-pyrazolo[3,4-b]pyridine.

3. A pharmaceutical composition for treatment of inflammation, pain, fever, allergy, arthritis, rheumatism and platelet aggregation which comprises, an antiinflammatory, analgesic, antipyretic, antiallergic, antiarthritic, antirheumatic and platelet aggregation inhibitory effective amount, respectively, of the pyrazolopyridine compound or pharmaceutically acceptable salt thereof as defined in claim 1, and a pharmaceutically acceptable additive therefor.

4. A method of treating inflammation, pain, fever, allergy, arthritis, rheumatism and platelet aggregation comprising administering to a subject in need of treatment an antiinflammatory, analgesic, antipyretic, antiallergic, antiarthritic, antirheumatism and platelet aggregation inhibiting effective amount, respectively, of the pyrazolo-pyridine compound or pharmaceutically acceptable salt thereof as defined in claim 1.

* * * * *